(12) United States Patent
Jones et al.

(10) Patent No.: US 8,475,846 B2
(45) Date of Patent: Jul. 2, 2013

(54) COLORED MICACEOUS PIGMENTS HAVING BISMUTH OXYCHLORIDE APPEARANCE AND PERFORMANCE EFFECTS

(75) Inventors: Steven Alan Jones, Budd Lake, NJ (US); Gabriel E. Uzunian, Rye, NY (US); Betty F. Aucar, Ossining, NY (US)

(73) Assignee: BASF Corporation, Florham Park, NJ (US)

( * ) Notice: Subject to any disclaimer, the term of this patent is extended or adjusted under 35 U.S.C. 154(b) by 289 days.

(21) Appl. No.: 12/720,035

(22) Filed: Mar. 9, 2010

(65) Prior Publication Data

US 2011/0223218 A1 Sep. 15, 2011

(51) Int. Cl.
*A61K 9/14* (2006.01)
(52) U.S. Cl.
USPC ............... 424/490; 424/400; 424/489
(58) Field of Classification Search
None
See application file for complete search history.

(56) References Cited

U.S. PATENT DOCUMENTS

| | | | |
|---|---|---|---|
| 2,995,459 A | 8/1961 | Soloway | |
| 3,087,828 A | 4/1963 | Linton | |
| 3,087,829 A | 4/1963 | Linton | |
| 3,822,141 A | 7/1974 | Kaufman | |
| 3,926,559 A | 12/1975 | Stevens | |
| 3,926,659 A | 12/1975 | Bernhard et al. | |
| 3,951,679 A | 4/1976 | Bernhard et al. | |
| 3,980,491 A | 9/1976 | Eberts | |
| 4,084,983 A | 4/1978 | Bernhard et al. | |
| 4,146,403 A | 3/1979 | Armanini et al. | |
| 4,192,691 A | 3/1980 | Armanini | |
| 4,309,480 A | 1/1982 | Armanini | |
| 4,744,832 A | 5/1988 | Franz et al. | |
| 4,755,229 A | 7/1988 | Armanini | |
| 5,260,068 A * | 11/1993 | Chen | 424/451 |
| 5,273,576 A | 12/1993 | Sullivan et al. | |
| 5,344,488 A | 9/1994 | Reynders et al. | |
| 5,433,779 A | 7/1995 | DeLuca, Jr. | |
| 5,456,749 A | 10/1995 | Iwasa et al. | |
| 5,885,342 A | 3/1999 | Gale et al. | |
| 5,958,125 A | 9/1999 | Schmid et al. | |
| 6,129,784 A | 10/2000 | Ikuta et al. | |
| 6,579,357 B1 | 6/2003 | Cao | |
| 6,719,838 B2 | 4/2004 | Heider et al. | |
| 6,875,264 B2 | 4/2005 | Zimmermann et al. | |
| 6,899,757 B2 | 5/2005 | Chang et al. | |
| 7,014,700 B2 | 3/2006 | DeLuca, Jr. et al. | |
| 7,241,503 B2 | 7/2007 | Noguchi | |
| 2003/0211058 A1 | 11/2003 | Matts et al. | |
| 2005/0214236 A1 | 9/2005 | Peng et al. | |
| 2007/0048237 A1 | 3/2007 | Song et al. | |
| 2008/0014321 A1 * | 1/2008 | Schweinfurth et al. | 426/250 |

FOREIGN PATENT DOCUMENTS

JP 2001-279126 10/2001

* cited by examiner

*Primary Examiner* — Robert A Wax
*Assistant Examiner* — Melissa Mercier
(74) *Attorney, Agent, or Firm* — Anna-Lisa Gallo

(57) ABSTRACT

A combination pigment having a mica and/or metal oxide-coated mica substrate, an absorption colorant coating, and a waxy film bonding the absorption colorant coating to the substrate.

18 Claims, No Drawings

COLORED MICACEOUS PIGMENTS HAVING BISMUTH OXYCHLORIDE APPEARANCE AND PERFORMANCE EFFECTS

FIELD OF THE INVENTION

This invention deals with colored nacreous pigments and with processes for producing these pigments.

BACKGROUND OF THE INVENTION

Nacreous pigments produce pearl-like, metallic, and iridescent effects. Natural pearl essence, a mixture of guanine and hypoxanthine obtained from the scales of fish, has long been used in cosmetic formulations. Synthetic nacreous pigments developed for cosmetic use include mica-based pigments and bismuth oxychloride, or bismuth oxychloride-mica. Muscovite mica platelets coated with a metallic oxide, such as titanium dioxide have been widely used. A relatively thin titanium dioxide coating produces a pearl-like or silvery luster. Mica platelets with thicker coatings produce color, even though the components are colorless, through the phenomenon of light interference; they are known as interference pigments. The color, called the reflection color, is seen most effectively by specular or mirror-like reflection, where the angle of reflection equals the angle of incidence. The reflection color is a function of optical thickness, i.e. the geometrical thickness times the refractive index, of the coating. Optical thickness of about 100 nm to about 160 nm produce reflections which may be called white, silvery or pearly; optical thickness of about 190 nm or more produce colored reflections.

Nacreous or pearlescent pigments containing mica or mica coated with titanium dioxide are known in the art. Reference is made, e.g., to U.S. Pat. Nos. 3,087,828 3,926,659; 4,146,403; 4,192,691; 4,744,832; 5,273,576; 5,433,779; 5,456,749; and 6,899,757. Each of these patents is incorporated by reference herein in its entirety.

The bismuth oxychloride-mica powders have the advantage of softness, good compressibility and high luster. Bismuth oxychloride-mica pigments are made by precipitating bismuth oxychloride crystals in the presence of mica. In general terms, this is accomplished by hydrolyzing a soluble bismuth compound in an aqueous slurry of mica. While there are a number of ways of accomplishing this, a preferred procedure is to first prepare an acidic slurry of wet ground mica to which is added a solution of a soluble bismuth salt. The bismuth compound hydrolyses to form a bismuth oxychloride precipitate. The acidity of the system is maintained by adding a solution of a base, such as sodium hydroxide, for neutralization of the acid formed by the hydrolysis reaction. The amount of the bismuth solution is controlled so as to obtain the desired ratio of BiOCl to mica, generally in the range of 1:4 to 4:1, preferably 1:1.5 to 1.5:1. Reference is made to U.S. Pat. No. 3,980,491 regarding preparation of BiOCl pigments. The appearance and feel of bismuth oxychloride pigments make these pigments popular with consumers. However, these pigments have been perceived by some consumers to cause skin irritation. Consequently, it has become desirable to develop non-BiOCl pigments which have the luster and feel of BiOCl pigments.

Combination pigments are mare complex than the mica-based and BiOCl interference pigments. In combination pigments, the oxide-coated mica pigment is further coated with an absorption pigment or dye, so-called because it absorbs some portion of the visible spectrum. If the absorption colorant has the same hue as the reflection color of the oxide-mica pigment, that color is intensified and is seen over a wide range of angles; if it has a different hue, the reflection color or a color close to it is seen at the specular angle, whereas the hue of the absorption pigment is seen at other angles. In some cases, transition colors may be seen between the extremes. Thus a single pigment has more than one color. The absorption colorant coat should be uniform and should adhere firmly to the oxide-coated mica particles.

In known combination pigments, the desired results are achieved by depositing the colorant or a precursor on the pigment platelets from aqueous solution. For example, U.S. Pat. No. 4,309,480 teaches that iron blue (ferric ferrocyanide) may be precipitated onto $TiO_2$-coated mica by the reaction of ferric chloride and potassium ferrocyanide in aqueous solution. Aluminum hydroxide may be precipitated after the iron blue or simultaneously with it, but it is not required for the formation of the iron blue coating. U.S. Pat. No. 3,951,679 shows that an Fe(II) phosphate layer may be precipitated onto mica pigments from aqueous solution and then converted in place to ferrous ferrocyanide by reaction with ferrocyanide solution, followed by oxidation in place to ferric ferrocyanide. U.S. Pat. No. 4,084,983 describes the formation of colored lakes on mica pigments by first depositing aluminum hydroxide on the surface from soluble reactants and then reacting with a dye in solution. Other combination pigments and methods of manufacturing same are disclosed in U.S. Pat. Nos. 5,885,342 and 6,129,784.

In U.S. Pat. No. 4,755,229, a combination pigment is prepared by providing an aqueous dispersion of the colored pigment containing an anionic polymeric substance, such as albumin or xanthan gum, and adding the dispersion to a suspension of the mica or oxide-coated mica pigment. The hydrous oxide of a polyvalent metal, for example chromium (III) or aluminum(III), is then produced by the simultaneous addition of a solution of the metal salt and of a basic solution. The dispersed pigment particles and the polymer deposit with the hydrous oxide of the polyvalent metal to form a smooth, adherent, uniform coating on the mica platelets. It is believed that the polymer reacts with the polyvalent metal to form a complex hydrous oxide.

The appearance and feel of mica or titanium-dioxide-coated-mica pigments are perceived by consumers to be inferior to those of BiOCl pigments. Accordingly, it is desirable to provide mica and titanium-dioxide-coated mica pigments having the appearance and feel of bismuth oxychloride. Until the present invention, mica-based pigments have not been provided with the look, e.g. optical properties, and feel of BiOCl pigments.

SUMMARY OF THE INVENTION

In the present invention, an aqueous dispersion of a colored metal oxide pigment and a wax or mixture of waxes is added to a suspension of mica and/or oxide-coated mica platelets to coat the platelets with the color absorbent pigment. The wax bonds the colored metal oxide to the mica platelet without the need of reactants to form the adsorption colorant and attach the colorants onto the mica or oxide-coated mica surface.

DETAILED DESCRIPTION OF THE INVENTION

Coated mica pigments are now well known and widely used to produce pearlescent, metallic, and iridescent effects. Colorless oxides, such as $TiO_2$ and $ZrO_2$, are described as coatings for mica in U.S. Pat. No. 3,087,828. Colored oxides, such as $Fe_2O_3$, $Cr_2O_3$, etc., appear in U.S. Pat. No. 3,087,829.

Interference pigments of a colorless oxide coated on mica are of particular interest, because the color is derived entirely from the interference effect. They make possible combination pigments with the widest range of colors: any desired reflection color is obtainable by controlling the thickness of the oxide coating, and absorption pigments of any desired color are available for overcoating. For example, a blue-reflecting $TiO_2$-coated mica overcoated with a red absorption colorant appears blue at the specular angle and primarily red at other angles. If the oxide coating consists of or includes a colored oxide, the pigment itself already has a reflection color and an absorption color; the latter modifies the color of the absorption pigment overcoating.

In some cases, the absorption colorant can shift the hue of the reflection color to some extent. This factor is taken into account in deciding on the thickness of the oxide coating to be deposited on the mica.

The procedure is effective on uncoated mica as well as oxide-coated mica and hydrous oxide-coated mica. The oxide coatings may be of $TiO_2$, $ZrO_2$, $SnO_2$, ZnO, $Fe_2O_3$, $Cr_2O_3$, $V_2O_5$, and the hydrous forms thereof. The oxide may be present in various crystalline forms, for example, $TiO_2$ can be anatase or rutile. Combinations of oxides of two or more metals may be used. The colorless oxides allow the greatest freedom in choice of absorption colorant; the color of the colored oxides influences the choice of absorption colorant because the final absorption color is determined by the mixture of the two colors.

The oxide coating typically has an optical thickness from about 40 to about 600 nm. The mica platelets are from about 3 to about 100 microns, including from about 5 to about 35 microns in their longest direction, and from about 0.1 to 5 microns in thickness, including about 0.5 micron. In addition, the mica flakes or particles used in the present invention preferably have a specific surface area (BET) of about 1 to 10 $m^2/g$, more preferably about 2 to 6 $m^2/g$.

Suitable types of mica for the micaceous pigments of the invention are muscovite, phlogopite, biotite, and synthetic micas. Muscovite is the preferred natural mica because its own light color does not adversely affect the color of the absorption pigment.

Suitable mica flakes and titanium dioxide coated mica flakes which can be used in the present invention include those which are known in the art. Reference is made, e.g., to are disclosed, e.g., in U.S. Patent Nos. e.g., to U.S. Pat. Nos. 3,087,828; U.S. Pat. Nos. 3,926,659; 4,146,403; 4,192,691; 4,744,832; 5,273,576; 5,433,779; 5,456,749; and 6,899,757; which were previously incorporated by reference herein.

In order to utilize an insoluble absorption pigment successfully in combination pigments, it is desirable that the insoluble pigment be very highly dispersed. A convenient starting point is the dry pigment or preferably an aqueous presscake of the pigment. After dilution with water or other liquid, such as alcohol, dispersion is achieved by any one of the usual techniques, such as milling, high shear mixing, or application of ultrasonic energy. The desired degree of dispersion is similar to that conventionally used in paint and coating formulations.

The colorant coating preferably contains one or more absorbent colorants in the form of metal oxides, hydroxides or hydrates. Typical color absorbent metal oxides include $ZrO_2$, $SnO_2$, $ZnO_2$, $Fe_2O_3$, $Cr_2O_3$, $V_2O_5$, etc. A particularly useful absorbent colorant is an iron-containing colorant, e.g., ferric hydroxide and/or iron oxides. Suitable iron oxides include those disclosed in, for example, in U.S. Published Application No. 2007/0048237 and U.S. Pat. Nos. 3,087,828; 3,926,559; 5,273,576; 5,433,779; and 7,241,503; all of which are incorporated by reference herein in their entirety. An absorbent colorant coating composed of a blend of iron oxide colorants, e.g., a blend of red iron oxide, black iron oxide and yellow iron oxide yields a desirable combination pigment. Any mixture of absorbent colorants can be utilized and there is no intention to limit the present invention by mention of specific mixtures.

Any absorption colorants which are water insoluble and which may be highly dispersed in water or water-alcohol are suitable for the invention. Besides the metal oxides described above, absorption colorants also include, for example, carbon black and organic pigments in the following groups: azo compounds, anthraquinones, perinones, perylenes, quinacridones, thioindigos, dioxazines, and phthalocyanines and their metal complexes.

The absorption colorants, depending on their color intensity, are used in a concentration range of about 0.01% to about 30% based on the weight of mica pigment, preferably 0.1% to 20%. The term "mica pigment" is meant to include uncoated mica platelets, metal oxide coated mica and mixtures thereof. In general, the insoluble absorption colorants will have a particle size of from about 10 nm to 10 microns, typically 100 nm to 5 microns, including 400 nm to 2 microns.

To bond the absorbent colorant coating to the mica pigment, a wax material is added to the aqueous dispersion of mica pigment and insoluble colorant. The wax materials useful in the present invention include natural and synthetic waxes, including saturated and unsaturated hydrocarbons, natural or synthetic fatty acids of $C_{12}$-$C_{40}$, preferably $C_{12}$-$C_{22}$, more preferably $C_{16}$-$C_{18}$, carbon chain length and mixtures thereof, including esters and salts thereof, fatty alcohols and fatty ethers of $C_9$-$C_{24}$, carbon length. Useful fatty acids include, e.g., myristic, palmitic, stearic, oleic, linoleic, linolinic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed, rosin acids and greases. Preferred fatty acid waxy agents are sodium stearate, sodium palmitate, potassium stearate, potassium palmitate, sodium myristate, aluminum monostearate and mixtures thereof. Most are alkali metal fatty acids such as sodium stearate.

Additional waxes for use in the present invention include, e.g., aliphatic fatty alcohols having a $C_{10-22}$ carbon chain, polyoxyethylene fatty alcohol ethers, polyoxyethylene fatty acid esters, alkylphenol polyglycol ethers, and hydroxyalkyl cellulose, e.g., hydroxypropylcellulose. A useful wax used in this invention is a mixture of cetearyl alcohol and ceteareth 20. Suitable mixtures of cetearyl alcohols and ceteareth-20 are disclosed, e.g., in U.S. Published Application Nos. 2003/0211058 and 2005/0214236, both of which are incorporated by reference herein in their entirety. A mixture of cetearyl alcohol and ceteareth-20 which can be used in the present invention is commercially available from Lubrizol under the designation "Promulgen™ D." Promulgen™ D is a nonionic emulsifier in the form of a waxy solid and is composed of ethoxylated cetearyl alcohol compounded with cetearyl alcohol.

In general, the waxy material bonding agent will be provided in amounts of 0.4% to 5% by weight based on the weight of the mica pigment present in the slurry.

Broadly, the combination pigments of this invention are made by forming a slurry of the mica and/or titanium-dioxide-coated substrate with deionized water and combining the slurry with sequentially added aqueous dispersions of the colorant(s), wax(es) and, optionally, a precipitating agent(s).

Again, mixtures of absorption colorants and mixtures of waxes can be used. Precipitating agents, such as calcium chloride, aids in breaking the dispersion and improving separation of the colorant and wax from the aqueous dispersion and bonding the absorption colorant to the mica pigment. In general, the precipitating agents will be present in amounts of from about 0.1 to 3.0% based on the weight of the mica pigments contained in the slurry.

Specifically, the combination pigments of this invention can be prepared by combining the mica pigment with water (preferably deionized water) and stirring so as to form a slurry. The pH of the slurry is adjusted to a value within the range of 5.0 to 9.0 using a suitable acid or base. Next, a dispersion of the absorption colorant(s) is prepared by blending at least one colorant with water (preferably deionized water) or water/alcohol mixture. Improved dispersment of the colorant in the aqueous carrier can be achieved as described above. The dispersion is then added to the mica pigment slurry. A solution or emulsion of the waxy bonding agent is prepared by dissolving the wax in water (deionized water). For example, if the wax is sodium stearate, it is dissolved in hot (80-90° C.) water. This solution is added to the slurry and stirred. An aqueous solution of a precipitating agent can then be added to the slurry. Non-limiting examples of suitable precipitating agents include, e.g., alkali metal hydroxides of sodium, potassium, and the like; and alkaline earth metal salts of calcium, magnesium and the like. As alkaline earth metal salts of calcium or magnesium, chlorides, hydrochlorides and nitrates thereof can be used. Calcium chloride is the preferred precipitating agent used in the method of the present invention. After stirring for 15 minutes to 2 hours, the final slurry can be filtered and the filter cake is then dried and screened. The obtained pigment product contains a mica and/or metal oxide coated mica substrate having a coating of absorption colorants attached thereto via the film formed from the waxy agent.

The combination pigments of this invention can be used in any application where effect pigments have been used heretofore. Such uses are disclosed, e.g., in U.S. Pat. Nos. 3,926,659; 6,719,838; 6,875,264; 7,014,700 and 7,241,503, each of which is incorporated by reference herein in its entirety. The pigments of this invention can be used, e.g., in paints, plastics, inks, printing, cosmetics, dopants for laser marking, non-dusting pigment products, cosmetics and personal care products. The pigments of this invention are preferably useful to color cosmetic formulations. Thus, it has been found that the combination of pigments of this invention have the look and feel of BiOCl interference pigments with the irritation possible with using BiOCl materials.

From the foregoing description, one skilled in the art can easily ascertain the essential characteristics of this invention, and without departing from the spirit and scope thereof, can make various changes and modifications of the invention to adapt it to various usages and conditions.

EXPERIMENTAL

The following examples are set forth in order to further illustrate the invention but are not intended to limit it. Throughout this specification and claims, all parts and percentages are by weight and all temperatures and degrees are Centigrade unless otherwise indicated.

Example 1

In a 19 L beaker, 1350 grams of a titanium-dioxide-coated mica (average particle size 32 µm) was slurried in 6170 mL of deionized water and stirred at 170 rpm at room temperature. The pH was adjusted to 6.75 using 10% acetic acid. A pigment dispersion was prepared by blending 123.12 grams of yellow iron oxide, 70.20 grams of black iron oxide, and 159.84 grams of red iron oxide into 1 liter of deionized water using a kitchen blender on the highest speed for 8 minutes. This pigment dispersion was added to the slurry at 34 mL/min. A solution of sodium stearate was prepared by dissolving 17.28 grams in 490 mL of hot (80-90° C.) deionized water. This solution was added to the slurry at 17 mL/min. After a 30 minute stir time, a solution of 3.65 grams of calcium chloride in 430 mL of deionized water was then added to the slurry at 14.5 mL/min. Next, 16.69 grams of Promulgen D were dissolved in 430 mL of deionized water and added to the slurry at 14.9 ml/min. After a 30 minute stir, the final slurry was filtered, but not washed. The filtercake was then dried at 75° C. for 24 hours and then screened.

Example 2

The procedure of Example 1 was repeated except that the titanium-dioxide-coated mica had an average particle size of about 5 µm.

Example 3

The procedure of Example 2 was repeated except for the following differences: i) uncoated mica having an average particle size of 5 µm was used instead of titanium dioxide coated mica; ii) 1113.75 grams of the mica were slurried in a total of 170 mL of deionized water; iii) the pigment dispersion was prepared by blending 184.68 grams of yellow iron oxide, 105.30 grams of black iron oxide, and 239.76 grams of red iron oxide into 1.5 L of deionized water; iv) the solution of sodium stearate was prepared by dissolving 25.92 grams in 735 mL of hot (80-90° C.) deionized water; v) the calcium chloride solution was prepared by dissolving 5.48 grams in 645 mL of deionized water; and vi) the Promulgen D solution was prepared by dissolving 25.04 grams in 645 mL of deionized water.

Example 4

The procedure of Example 3 was repeated except that the initial slurry contained 1049.61 grams of uncoated mica with an average particle size of 5 µm and 116.62 grams of a titanium dioxide coated mica with an average particle size of 5 µm.

Example 5

The procedure of Example 3 was repeated except that the initial slurry contained 979.12 grams of uncoated mica with an average particle size of 5 µm and 244.78 grams of a titanium dioxide coated mica with an average particle size of 5 µm.

Example 6

A solution of 3.33 grams of calcium chloride in 1214 mL of deionized water was prepared in a 3 L Morton flask and stirred at 500 rpm. To this solution, 150 grams of the product from Example 4 were slowly added. After the pH was adjusted to 6.0, a solution of 4.5 grams of lauroyl lysine dissolved in 166 mL of 3% NaOH was added to the slurry at 3.8 mL/min while the pH was held constant with 10% NaOH.

After 20 minutes of addition, the stir rate was lowered to 400 rpm. Following the addition, the slurry was filtered and washed 2 times with 1500 mL of deionized water. The resulting filtercake was dried at 75° C. for 24 hours and then screened.

Example 7

The procedure carried out in Example 6 was repeated except that the product from Example 5 was used instead of the product from Example 4.

Example 8

The procedure carried out in Example 1 was repeated except that: i) the initial slurry contained 1020 grams of uncoated mica with an average particle size of 32 μm and 180 grams of a titanium-dioxide-coated mica with an average particle size of 32 μm; and ii) 300 grams of titanium dioxide pigment were used instead of iron oxide pigments.

Example 9

The procedure followed in Example 8 was repeated except for the following: i) the initial slurry in Example 9 contained 375 grams of uncoated mica with an average particle size of about 9 μm and 750 grams of a titanium-dioxide-coated mica with an average particle size of about 9 μm; ii) the pigment dispersion in Example 9 was prepared by blending 375 grams of titanium dioxide pigment into 1.25 L of deionized water; iii) the solution of sodium stearate was prepared by dissolving 21.6 grams in 613 mL of hot (80-90° C.) deionized water; iv) the calcium chloride solution was prepared by dissolving 4.56 grams in 538 mL of deionized water; and v) the Promulgen D solution was prepared by dissolving 20.86 grams in 538 mL of deionized water.

Example 10

The procedure followed in Example 1 was repeated except for the following: i) the initial slurry in Example 10 contained 732 grams of uncoated mica with an average particle size of 9 μm and 300 grams of a titanium-dioxide-coated mica with an average particle size of 9 μm. The pigment dispersion was prepared by blending 163.5 grams of yellow iron oxide, 63.0 grams of black iron oxide, and 241.5 grams of red iron oxides into 1325 mL of deionized water; the solution of sodium stearate was prepared by dissolving 22.90 grams in 649 mL of hot (80-90°) deionized water; iii) the calcium chloride solution was prepared by dissolving 4.84 grams in 570 mL of deionized water; and iv) the Promulgen solution was prepared by dissolving 22.12 grams in 570 mL of deionized water.

Example 11

The procedure followed in Example 1 was repeated in Example 8 except that: i) the initial slurry contained 225 grams of uncoated mica with an average particle size of 9 μm and 1050 grams of a titanium-dioxide-coated mica with an average particle size of 5 μm; ii) the pigment dispersion in Example 11 was prepared by blending 225 grams of titanium dioxide pigment into 750 mL of deionized water; iii) solution of sodium stearate was prepared by dissolving 12.96 grams in 368 mL of hot (80-90° C.) deionized water; iv) the calcium chloride solution was prepared by dissolving 2.74 grams in 323 mL of deionized water; and v) the Promulgen D solution was prepared by dissolving 12.52 grams in 323 mL of deionized water.

Example 12

This example was run like Example 10 except that the pigment dispersion was prepared by blending 468 g of yellow iron oxide into 1500 mL of de-ionized water.

Example 13

This example was run like Example 10 except that the pigment dispersion was prepared with 468 g of red iron oxide.

Example 14

This example was run like Example 10 except that the pigment dispersion was prepared with 42.55 g of red iron oxide and 425.45 g of black iron oxide.

Example 15

This example was run as a cosmetic formulation for concealer stick

| Ingredients | % w/w |
|---|---|
| Phase A. | |
| Beeswax (White Beeswax) (available from Koster Keunen, LLC) | 9.0 |
| Hydrogenated Olive Oil (and) *Olea Europaea* (Olive) Fruit Oil (and) *Olea Europaea* (Olive) Fruit Oil Unsaponifiables (Oliwax) (available from B&T Company) | 12.0 |
| *Copernicia Cerifera* (Carnauba) Wax (CARNAUBA T-3) (available from Koster Keunen, LLC) | 3.0 |
| *Crambe Abyssinica* Seed Oil (and) *Butyrospermum Parkii* (Shea Butter) Extract (FANCOL ABYSHEA) (available from Fancor Ltd). | 15.0 |
| Meadowfoam Estolide (Fancor Meadowestolide) (available from Fancor Ltd) | 3.0 |
| *Prunus Amygdalus* Dulcis (Sweet Almond) Oil (JEEN Sweet Almond Oil) (available from Jeen International Corp.) | 12.0 |
| *Ricinus Communis* (Castor) Seed Oil (Castor Oil) (available from Alzo International Inc.) (q.s. to 100%) | 6.0 |
| Luvitol ® Lite (Hydrogenated Polyisobutene) (available from BASF Corp.) | 10.0 |
| Phase B. | |
| *Crambe Abyssinica* Seed Oil (FANCOR ABYSSINIAN OIL) (available from Fancor Ltd) | 10.0 |
| Cloisonne ® Satin Gold 262MC (Mica (and) Titanium Dioxide (and) Iron Oxides)) (available from BASF Corp.) | 10.0 |
| The product from Example 11 | 6.0 |
| The product from Example 10 | 4.0 |
| Antioxidants | q.s. |
| UV Absorbers | q.s. |
| Preservatives | q.s. |

Procedure

I. Pre-dispersed Phase B

II. Weighed all Phase A ingredients in a vessel and heated to 85±3° C., stirred until melted and uniform.

III. Add premixed Phase B to Phase A, maintained temperature at 82±3° C. for 30 minutes with gentle agitation. (This will allow de-aeration if vacuum is not available).

IV. Reduced temperature to 75±3° C.
V. Poured into molds.

Example 16

This example was a cosmetic formulation for a cream foundation

| Ingredients | % w/w |
|---|---|
| Phase A. | |
| DI Water (q.s to 100%) | 48.863 |
| Methylpropanediol (MPDiol glycol) (available from Lyondell Chemical Co.) | 5.000 |
| Magnesium Aluminum Silicate (VEEGUM) (available from RT Vanderbilt, Inc.) | 0.600 |
| Xanthan Gum (KELTROL CG-T) (available from CP Kelco) | 0.400 |
| Phase B. | |
| Cetearyl Olivate (and) Sorbitan Olivate (OLIVEM 1000) (available from B&T Company) | 4.000 |
| Hydrogenated Olive Oil (and) *Olea Europaea* (Olive) Fruit Oil (and) *Olea Europaea* (Olive) Oil Unsaponifiables (OLIWAX) (available from B&T Company) | 2.000 |
| Caprylic/Capric Triglyceride (and) Di-PPG-3 Myristyl Ether Adipate (and) Sorbitan Isostearate (CRODASPERSE) (available from CRODA) | 7.000 |
| Meadowfoam Estolide (and) Meadowfoam Delta-Lactone (MEADOWDERM 100) (available from Fancor Ltd.) | 2.000 |
| Isodecyl Neopentanoate (CERAPHYL SLK) (available from ISP) | 5.000 |
| Antioxidants | q.s. |
| Preservatives | q.s. |
| Phase C. | |
| Kaolin (HUBER 90) (available from J. M. Huber Corp.) | 0.500 |
| Polymethyl Methacrylate (PMMA H) (available from Brenntag Speialties, Inc.) | 4.000 |
| Titanium Dioxide | 3.137 |
| Mearlmica ® SVA (Mica (and) Lauroyl Lysine) (available from BASF Corp.) | 3.000 |
| The product from Example 11 | 1.000 |
| The product from Example 10 | 0.500 |
| Phase D. | |
| DI Water | 10.000 |
| Chione ™ Snowfall White S130D (Synthetic Fluorphlogopite (and) Titanium Dioxide) (available from BASF Corp.) | 3.000 |

Procedure

I. Added DI Water and MPDiol glycol to main vessel and began homogenization.
II. Sprinkled in VEEGUM and homogenized until uniform.
III. Sprinkled in the KELTROL CG-T and homogenized until uniform.
IV. In a separate container, heated Phase B to 60-70° C. and mixed until uniform.
V. Under homogenization added Phase B to Phase A at 70° C.
VI. Pulverized Phase C in appropriate blending equipment.
VII. Under homogenization, sprinkled Phase C to Phase AB until uniform color was achieved. Then, sweep mixed.
VIII. Premixed Phase D and added to Phase ABC and began cooling batch.
IX. Dropped batch at 40° C.

Example 17

This example was a cosmetic formulation for a lipstick

| Ingredients | % w/w |
|---|---|
| Phase A. | |
| Beeswax (White Beeswax) (available from Koster Keunen, LLC) | 7.50 |
| Hydrogenated Olive Oil (and) *Olea Europaea* (Olive) Fruit Oil (and) *Olea Europaea* (Olive) Oil Unsaponifiables (OLIWAX) (available from B&T Company) | 10.00 |
| *Copernicia Cerifera* (Carnauba) Wax (CARNAUBA T-3) (available from Koster Keunen, LLC) | 2.50 |
| *Crambe Abyssinica* Seed Oil (and) *Butyrospermum Parkii* (Shea Butter) Extract (FANCOL ABYSHEA) (available from Fancor Ltd.) | 12.50 |
| *Prunus Amygdalus* Dulcis (Sweet Almond) Oil (JEEN Sweet Almond Oil) (available from Jeen International Corp.) | 10.00 |
| Meadowfoam Estolide (MEADOWESTOLIDE) (available from Fancor Ltd.) | 2.50 |
| *Ricinus Communis* (Castor) Seed Oil (Castor Oil) (available from Alzo International Inc.) | 5.00 |
| Phase B. | |
| *Crambe Abyssinica* Seed Oil (FANCOR ABYSSINAN OIL) (available from Fancor Ltd.) (q.s. to 100%) | 29.10 |
| The product from Example 11 | 2.50 |
| The product from Example 10 | 2.50 |
| Cloisonne ® Cerise Flambe 550Z (Mica (and) Titanium Dioxide (and) Iron Oxides) (available from BASF Corp.) | 15.00 |
| Vitamin E Acetate (Tocopheryl Acetate) (available from BASF Corp.) | 0.50 |
| Bisabolol rac. (Bisabolol) (available from BASF Corp.) | 0.40 |
| Preservatives | q.s. |
| Fragrance | q.s. |
| UV Absorbers | q.s. |

Procedure
I. Pre-dispersed Phase B.
II. Weighed all phase A ingredients in a vessel and heated to 85±3° C., stirring until melted and uniform
III. Added premixed Phase B to Phase A, maintained temperature at 82±3° C. for 30 minutes with gentle agitation. (This allowed de-aeration if vacuum is not available).
IV. Reduced temperature to 75±3° C. and added fragrance.
V. Poured into molds.

Example 18

This example was a cosmetic formulation for a pressed powder eye shadow

| Ingredients | % w/w |
|---|---|
| Phase A. | |
| The product from Example 10 | 15.00 |
| Sicovie Black 85 E 172 (Iron Oxides) (available from BASF Corp.) | 1.00 |
| The product from Example 11 | 5.00 |
| Mearimica ® SVA (Mica (and) Lauroyl Lysine) (available from BASF Corp.) (q.s. to 100%) | 35.50 |
| Kaolin (HUBER 90) (available from J. M. Huber Corp.) | 12.00 |
| Microcrystalline Cellulose (AVICEL PC 105) (available from FMC Corp.) | 10.00 |
| Phase B. | |
| *Crambe Abyssinica* Seed Oil (and) *Butyrospermum Parkii* (Shea Butter) Extract (FANCOL ABYSHEA) (available from Fancor Ltd.) | 10.50 |

-continued

| Ingredients | % w/w |
|---|---|
| *Simmondsia Chinensis* (Jojoba) Seed Oil (LIPOVOL J) (available from Lipo Chemicals, Inc.) | 2.10 |
| *Cocos Nucifera* (Coconut) Oil (Coconut Oil) (available from Jeen International Corp.) | 1.40 |
| Antioxidants | q.s. |
| UV Absorbers | q.s. |
| Preservatives | q.s. |
| Phase C. | |
| Flamenco ® Winter Sparkle 130Q (Mica (and) Titanium Dioxide) (available from BASF Corp.) | 5.00 |
| Reflecks ™ Shiny Gold G232Z (Calcium Sodium Borosilicate (and) Titanium Dioxide (and) Iron Oxides) (available from BASF Corp.) | 2.50 |

Procedure

I. Thoroughly blended Phase A in appropriate dry blending/dispersing equipment.
II. Sprayed Phase B into Phase A and pulverized until uniform.
III. Added Phase C and tumbled until uniform.
IV. Pressed.

Example 19

This example is a cosmetic formulation for a talc free mineral powder

| Ingredients | % w/w |
|---|---|
| Phase A. | |
| Mearlmica ® SVA (Mica (and) Lauroyl Lysine) (available from BASFCorp.) (q.s. to 100%) | 36.50 |
| Flamenco ® Summit Red R30D (Mica (and) Titanium Dioxide) (available from BASF Corp.) | 12.00 |
| Z-Cote ® Max (Zinc Oxide (and) Dimethoxydiphenylsilane/Triethoxycaprylylsilane Crosspolymer) (available from BASF Corp.) | 15.00 |
| The product from Example 11 | 6.50 |
| The product from Example 10 | 20.00 |
| Boron Nitride Powder (Boron Nitride) (available from ESK Ceramics) | 5.00 |
| Phase B. Luvitol ® Lite (Hydrogenated Polyisobutene) (available from BASF Corp.) | 2.50 |
| Octyldodecyl Neopentanoate (Elefac 1-205) (available from Alzo International, Inc.) | 2.50 |
| Antioxidants | q.s. |
| Preservatives | q.s. |

Procedure

I. Thoroughly blended Phase A in appropriate dry blending/dispersing equipment.
II. Pre-dispersed Phase B and spray into Phase A.
III. Pulverized and packaged into appropriate containers.

While the present invention has been particularly described, in conjunction with specific embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed:

1. A combination pigment comprising:
an interference mica pigment and
a coating of one or more absorption colorant bonded to the mica pigment by at least one waxy material,
wherein said absorption colorant has a particle size of about 10 nm to about 10 microns,
wherein the waxy material is a salt of a fatty acid.

2. The pigment according to claim 1, wherein said absorption colorant has a particle size of about 100 nm to 5 microns.

3. The pigment according to claim 1, wherein said absorption colorant is water insoluble.

4. The pigment according to claim 1, wherein the fatty acid has a $C_{12}$-$C_{40}$, carbon chain length.

5. A combination pigment comprising:
an interference mica pigment and
a coating of one or more absorption colorant bonded to the mica pigment by at least one waxy material,
wherein said absorbant colorant has a particle size of about 10 nm to about 10 microns,
wherein said waxy material is a mixture of at least two waxy materials,
wherein said waxy material is selected from natural and synthetic hydrocarbons, fatty acids, fatty esters, fatty alcohols, fatty ethers and salts thereof,
wherein at least one of the waxy material is a salt of a fatty acid.

6. The pigment according to claim 1, wherein the mica pigment comprises metal oxide-coated mica.

7. The pigment according to claim 1, wherein the mica pigment is uncoated mica.

8. The pigment according to claim 1, wherein the mica pigment is a blend of uncoated mica and metal oxide-coated mica.

9. The pigment according to claim 6, wherein said mica pigment comprises $TiO_2$-coated mica.

10. The pigment according to claim 3, wherein said absorption colorant comprises a metal oxide.

11. The pigment according to claim 1, wherein the one or more absorption colorant comprise at least one iron oxide pigment.

12. The pigment according to claim 11, wherein said absorption colorant comprises a blend of at least two of yellow iron oxide, black iron oxide and red iron oxide.

13. The pigment according to claim 1, wherein said absorption colorant comprises from about 0.01 to 50.0% based on the weight of the combination pigment.

14. The pigment according to claim 13, wherein said absorption colorant comprises from about 10 to 40% based on the weight of the combination pigment.

15. A cosmetic formulation containing the combination pigment of claim 1.

16. A method of forming a combination pigment comprising:
forming an aqueous slurry containing an interference mica pigment, a water insoluble absorption colorant and a waxy binder material and
depositing said waxy binder material and said absorption colorant on said mica pigment,
wherein the waxy binder material a salt of a fatty acid.

17. The method of claim 16, wherein said interference mica pigment comprises metal oxide coated mica, uncoated mica or mixtures thereof.

18. The method of claim 16, wherein said absorption colorant comprises a metal oxide.

* * * * *